United States Patent
Wershofen et al.

(10) Patent No.: US 10,807,084 B2
(45) Date of Patent: Oct. 20, 2020

(54) SILICA-BASED ZINC CATALYSTS, THEIR PREPARATION AND USE IN THE ALKOXYCARBONYLATION OF AMINES

(71) Applicant: Covestro Deutschland AG, Leverkusen (DE)

(72) Inventors: Stefan Wershofen, Mönchengladbach (DE); Markus Dugal, Kempen (DE); Gernot Jaeger, Cologne (DE); Anton Vidal Ferran, Montbrió del Camp (ES); Jose Luis Nuñez Rico, Tarragona (ES)

(73) Assignee: Covestro Deutschland AG, Leberkusen (DE)

( * ) Notice: Subject to any disclaimer, the term of this patent is extended or adjusted under 35 U.S.C. 154(b) by 0 days.

(21) Appl. No.: 16/612,818

(22) PCT Filed: May 14, 2018

(86) PCT No.: PCT/EP2018/062312
§ 371 (c)(1),
(2) Date: Nov. 12, 2019

(87) PCT Pub. No.: WO2018/210711
PCT Pub. Date: Nov. 22, 2018

(65) Prior Publication Data
US 2020/0147594 A1 May 14, 2020

(30) Foreign Application Priority Data
May 15, 2017 (EP) ..................... 17170988

(51) Int. Cl.
B01J 31/22 (2006.01)
B01J 37/02 (2006.01)
C07C 269/04 (2006.01)
C07F 3/06 (2006.01)

(52) U.S. Cl.
CPC ....... B01J 31/2213 (2013.01); B01J 37/0203 (2013.01); C07C 269/04 (2013.01); C07F 3/06 (2013.01); B01J 2531/26 (2013.01); B01J 2540/10 (2013.01)

(58) Field of Classification Search
None
See application file for complete search history.

(56) References Cited

U.S. PATENT DOCUMENTS 4,268,683 A   5/1981 Gurgiolo

FOREIGN PATENT DOCUMENTS

| CA | 2072034 | | 12/1992 | |
|----|---------|---|---------|---|
| CN | 101269341 A | | 9/2008 | |
| CN | 102872912 | * | 1/2013 | ............. B01J 31/04 |
| CN | 102872912 A | | 1/2013 | |
| EP | 0065026 A1 | | 11/1982 | |
| EP | 1268409 B1 | | 11/2005 | |
| EP | 1255728 B1 | | 8/2006 | |
| WO | 9855450 | | 12/1998 | |

OTHER PUBLICATIONS

CN-102872912 (machine translation on May 11, 2020 from Google Patents).*
Huirache-Acuna, R. et al. Materials 2013, 6, 4139-4167.*
Baba et al, Catalytic Synthesis of Dimethyl toluene-2,4-dicarbamate by the Methoxycarbonylation of 2,4-Toluenediamine with Dimethyl Carbonate Using Zn(OAc)2•H2O, Science and Technology in Catalysis, 2002, pp. 149-152.
Wang, Yi et al, Efficient and recyclable heterogeneous zinc alkyl carboxylate catalyst for the synthesis of N-phenyl carbamate from aniline and dimethylcarbonate, Catal. Sci. Technol. 2015, 5, pp. 109-113.
Grego, Sandra et al, Phosgene-free carbamoylation of aniline via dimethyl carbonate, Pure Appl. Chem., vol. 84, No. 3, pp. 695-705, 2012.
Li, Fang et al, Investigation of supported Zn(OAc)2 catalyst and its stability in N-phenyl carbamate synthesis, Appl. Catal., A, 2014, 475, pp. 355-362.
Guo, Xingcui et al, Zinc Carboxylate Functionalized Mesoporous SBA-15 Catalyst for Selective Synthesis of Methyl-4,4'-di(phenylcarbamate), Catal. Lett., 2009, 128, pp. 405-412.
Pure & Appl. Chem., Recommendations for the Characterization of Porous Solids, vol. 66, No. 8, 1994, pp. 1739-1758, IUPAC technical report.
Braunauer, Stephen et al, Adsorption of Gases in Multimolecular Layers, J. Am. Chem. Soc., 1938, 60, pp. 309-319.
Barrett, Elliott P. et al, The Determination of Pore Volume and Area Distributions in Porous Substances. I. Computations from Nitrogen Isotherms, J. Am. Chem. Soc. 1951, 73, pp. 373-380.
International Search Report, PCT/EP2018/062312, dated Jul. 27, 2018, Authorized officer: Stefania Tabanella.

* cited by examiner

Primary Examiner — Clinton A Brooks
(74) Attorney, Agent, or Firm — Donald R. Palladino

(57) ABSTRACT

The present invention relates to silica-based heterogeneous zinc compounds which are suitable as catalysts in the reaction of amines with dialkyl carbonates to produce carbamates. The catalysts have the formula $[SiO_2]$—$CH_2$—CHR—X—COOZn[Y], wherein $[SiO_2]$ represents a silica carrier selected from the group consisting of ordered mesoporous silica and irregular amorphous narrow pore silica, R represents a moiety selected from the group consisting of hydrogen, —$CH_3$, and —$CH_2CH_3$, preferably hydrogen, X is an aliphatic chain of 2 to 11 carbon atoms that optionally comprises ether moieties and [Y] represents a mono anion. The invention is also directed towards a method for the preparation of the aforementioned compounds and towards method for the alkoxycarbonylation of amines.

15 Claims, No Drawings

SILICA-BASED ZINC CATALYSTS, THEIR PREPARATION AND USE IN THE ALKOXYCARBONYLATION OF AMINES

CROSS-REFERENCE TO RELATED APPLICATIONS

This application is a U.S. National Phase application under 35 U.S.C. § 371 of International Application No. PCT/EP2018/062312, filed May 14, 2018, which claims priority to European Patent Application EP17170988.4, filed May 15, 2017, which are each incorporated herein by reference.

FIELD

The present invention relates to silica-based heterogeneous zinc compounds which are suitable as catalysts in the reaction of amines with dialkyl carbonates to produce carbamates. The catalysts have the formula $[SiO_2]$—$CH_2$—$CHR$—$X$—$COOZn[Y]$, wherein $[SiO_2]$ represents a silica carrier selected from the group consisting of ordered mesoporous silica and irregular amorphous narrow pore silica, R represents a moiety selected from the group consisting of hydrogen, —$CH_3$, and —$CH_2CH_3$, preferably hydrogen, X is an aliphatic chain of 2 to 11 carbon atoms that optionally comprises ether moieties and [Y] represents a mono anion. The invention is also directed towards a method for the preparation of the aforementioned compounds and towards a method for the alkoxycarbonylation of amines.

BACKGROUND

Carbamates are valuable intermediates in the production of agrochemicals, dyes, pharmaceutical compounds and, in particular, aromatic isocyanates used in the synthesis of polyurethanes. Most relevant from a commercial point of view are carbamates derived from 4,4'-methylenediphenylamine (MDA), its isomers and/or homologues or mixtures of the aforementioned compounds as obtained by acid-catalysed condensation/rearrangement reaction of aniline and formaldehyde, as well as 2,4-toluenediamine (TDA) or technical mixtures of the two TDA isomers 2,4-TDA and 2,6-TDA (approximately 80/20 mixtures). The aforementioned aromatic amines are used in the preparation of methylene diphenyl diisocyanate (MDI) and toluene diisocyanate (TDI), which are the direct precursors of polyurethanes. At present these isocyanates are produced industrially by phosgenation of the corresponding amines, a process which employs a toxic reagent (phosgene) and leads to large amounts of hydrochloric acid as side-product.

In the prior art, processes are known for the production of carbamates based on the functionalization of aromatic amines Ar-$NH_2$ with organic carbonates $WOCO_2W$ in the presence of suitable catalysts, according to the following scheme:

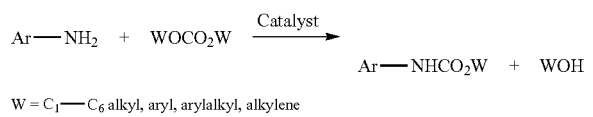

W = $C_1$—$C_6$ alkyl, aryl, arylalkyl, alkylene

In the case of aromatic diamines Ar(—$NH_2$)$_2$, biscarbamates are formed in a two-step reaction, with the corresponding monocarbamates being formed as intermediates, according to the following scheme:

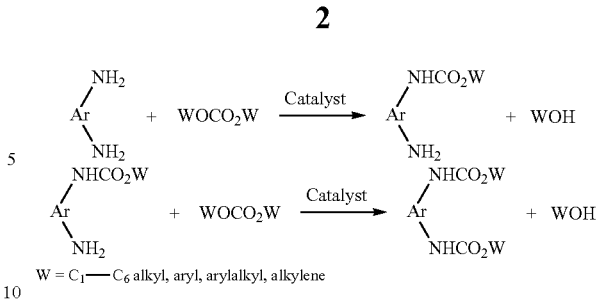

W = $C_1$—$C_6$ alkyl, aryl, arylalkyl, alkylene

Taking into account the alkylating properties of organic carbonates, N-alkylation competes with N-alkoxycarbonylation, and consequently N-alkylated products might be formed along the reaction, as well as products which are both N-alkylated and N-alkoxycarbonylated.

In the U.S. Pat. No. 4,268,683 and the European patent application EP-A-0065026 a process is disclosed for preparing carbamates from organic carbonates and aromatic amines in the presence of catalytic quantities of a Lewis acid catalyst. The catalyst should be soluble in the reaction mixture at the reaction conditions and be a member of the group consisting of a zinc or divalent tin halide, a zinc or divalent tin salt of a monovalent organic compound which has a pKa value of at least 2.8, and a zinc or divalent tin salt of trifluoroacetic acid. Among the zinc salts are mentioned: zinc chloride, zinc acetate, zinc acetate dihydrate, zinc oxyacetate ($(AcOZn)_2O$), zinc naphthenate, zinc octanoate, zinc propionate, zinc salicylate, zinc pivalate, zinc acrylate, zinc p-chlorobenzoate, zinc phenolate, zinc formate, zinc chloroacetate, zinc acetylacetonate, zinc oxalate, and zinc trifluoroacetate.

In the article of Baba et al., "Catalytic Synthesis of Dimethyl toluene-2,4-dicarbamate by the Methoxycarbonylation of 2,4-Toluenediamine with Dimethyl Carbonate Using $Zn(OAc)_2.H_2O$", Science and Technology in Catalysis, 2002, 149, the reaction of the amines MDA and TDA with dimethyl carbonate is described in the presence of a metal salt as catalyst to obtain the corresponding dicarbamates. Several salts of zinc, tin, lead and bismuth are mentioned. It is also disclosed that the selection of the metal salt is crucial for the formation of the carbamates. Among the catalysts some zinc carboxylates showed catalytic activity, while others were inactive. For instance, in the reaction of TDA with dimethyl carbonate, zinc acetate dihydrate as catalyst yielded 92% of dicarbamate, whereas zinc propionate yielded only 20% and zinc formate was completely inactive.

EP-A-1268409 describes the usage of zinc acetate dihydrate as catalyst in a continuous process for the manufacturing of aromatic carbamates by reaction of 80/20 mixtures of the two TDA isomers 2,4-TDA and 2,6-TDA with dimethyl carbonate. In EP-A-1255728, Zn salts such as zinc acetate or zinc acetate dihydrate (amongst other compounds) are mentioned as catalysts for the synthesis of aromatic carbamates by reaction of aromatic amines like 80/20 mixtures of the two TDA isomers 2,4-TDA and 2,6-TDA with dimethyl carbonate. Compounds or salts of Sn, Zn or Pb in particular are described as catalysts for the reaction of 2,4-TDA or technical mixtures of the two TDA isomers 2,4-TDA and 2,6-TDA with diethyl carbonate in EP-A-520273, or for the reaction of MDA (that is, 4,4'-MDA, its isomers and/or homologues or mixtures of the aforementioned compounds as obtained by acid-catalysed condensation/rearrangement reaction of aniline and formaldehyde) with dialkyl carbonates like dimethyl carbonate or diethyl carbonate in EP-A-510459.

*Catal. Sci. Technol.* 2015, 5, 109 (authors: Yi Wang and Bo Liu) describes a recyclable heterogeneous zinc alkyl carboxylate catalyst for the synthesis of N-phenyl carbamate from aniline and dimethylcarbonate. Wide pore mesoporous amorphous silica (pore size: 16.5 nm, specific surface area: 298 m²/g, pore volume 1.22 mL/g, particle size: 20-40 mesh) is mentioned as support.

CN 102872912 A discloses a catalyst for synthesizing methyl phenyl carbamate, a preparation method and an application method thereof; the preparation method comprising the following steps: performing a hydrosilylation addition reaction of silane compounds with hydrolysable groups and organic olefin acid ester compounds with a chain length of 3-11 carbons under the action of a catalyst, hydrolysing the product with a strong base, then performing neutralization with an acid, adjusting the pH value precisely to obtain an aqueous solution of the modifier; soaking wide pore spherical silica gel (pore size: 16.5 nm, specific surface area: 298 m²/g; believed by the inventors to be to the best of their knowledge amorphous) with an aqueous solution of the modifier, then drying the soaked silica gel, roasting in inert atmosphere, performing zinc ion exchange of the roasted sample, washing and drying to obtain the catalyst. The reaction of aniline and dimethyl carbonate in the presence of the catalyst is carried out at 100-230° C.

The catalyst described in *Catal. Sci. Technol.* 2015, 5, 109 and CN 102872912 A is derived from a silica carrier of comparatively high average pore diameter (significantly larger than 8.0 nm) and allows to produce methyl N-phenyl carbamate from aniline in up to 91.6% yield.

*Pure Appl. Chem.,* 2012, 84, 695 (authors: Sandra Grego, Fabio Arico, and Pietro Tundo) describes a phosgene-free carbamoylation of aniline with dimethyl carbonate in the presence of homogeneous, supported heterogeneous, and heterogeneous catalysts. Several heterogeneous catalysts were investigated. Basic zinc carbonate was shown to be the best catalyst.

*Appl. Catal., A* 2014, 475, 355 (authors: Fang Lia, Wenbo Lia, Jing Lib, Wei Xuea, Yanji Wanga, and Xinqiang Zhao) describes an investigation of supported $Zn(OAc)_2$ catalyst and its stability in N-phenyl carbamate synthesis.

WO 98/55450 A1 describes a method for the preparation of carbamates by reaction of aromatic amines with organic carbonates in the presence of a metal based catalyst on an inert carrier support. In particular, zinc salts of carboxylic acids on inert carriers such as silica are described.

*Catal. Lett.* 2009, 128, 405 (authors: Xingcui Guo, Zhangfeng Qin, Weibin Fan, Guofu Wang, Ruihua Zhao, Shaoyi Peng, and Jianguo Wang) describes a zinc carboxylate-functionalised mesoporous SBA-15 catalyst having a —(CH₂)₃— chain between the siliceous support and the carboxylate group for selective synthesis of methyl-4,4'-di (phenylcarbamate). The authors describe a final acid treatment of the catalyst ($H_2SO_4$ 48%, 95° C., 24 h), which makes the preparation method unsuitable for catalysts carrying any kind of acid-sensitive group, such as, for example, ether linkages (it is well established that aliphatic ether groups are cleaved to the corresponding alcohol groups in strong aqueous acid solutions, such as those employed in the final treatment described by the authors). Thus, zinc-based heterogeneous catalysts containing acid-sensitive groups, such as ether linkages, cannot be prepared with the synthetic steps described in that way.

CN 101269341 A relates to a catalyst used for synthesizing aromatic carbamates, the catalyst comprising an SBA-15-COOH molecular sieve in a range from 80 to 95 mass percent and zinc in a range from 5 to 20 mass percent. A specific and unequivocal structure of the catalysts employed is not disclosed. The authors refer to "SBA-15-COOH/SBA-15-COO(Zn)", which only indicates in a concise manner the catalytic groups (COO(Zn)) and the support (siliceous support SBA-15). The nature of the chain connecting these components of the catalyst is undefined.

SUMMARY

Taking into account the economic importance of carbamates as isocyanate precursors, it is highly desirable to provide further improvements regarding the catalyst-mediated preparation of carbamates. More specifically, carbamates should be prepared in high yield and with low amounts of by-products. The present invention addresses this need.

In one aspect, the present invention is directed to a silica-based zinc compound capable of serving as catalyst and having the general formula

wherein [SiO₂] represents a silica carrier selected from the group consisting of ordered mesoporous silica and irregular amorphous narrow pore silica, said silica carrier [SiO₂] being covalently bound to the terminal CH₂ group of "CH₂—CHR—X—COOZn[Y]";

R represents a moiety selected from the group consisting of hydrogen, —CH₃, and —CH₂CH₃, preferably hydrogen;

X is an aliphatic chain of 2 to 11 carbon atoms that optionally comprises ether moieties;

[Y] represents a mono anion.

Within the present invention, the term "ordered mesoporous silica" is understood to mean mesoporous silica (i.e. silica having an average pore diameter of from 2.0 nm to 50 nm, preferably of from >8.0 nm (in particular 9.0 nm) to 50 nm) with a defined pore structure, preferably a two-dimensional hexagonal channelled structure.

Within the present invention, the term "irregular amorphous narrow pore silica" is understood to mean porous silica gel of irregular shape and a non-ordered pattern of pores within the material and an average pore diameter of from 2.0 nm to 8.0 nm.

Within the present invention, the term "mono anion" is understood to mean an organic or inorganic compound or moiety bearing an overall charge of −1.

In the context of this invention, all values for "average pore diameter" are to be understood as referring to values as determined by the Barret-Joyner-Halenda (BJH) method, as described in more detail later on in this description (see no. II below).

In another aspect, the invention is directed to a method for preparing a silica-based zinc compound comprising the steps of:

A) Reacting an unsaturated carboxylic acid of the formula $CH_2=CR$—X—COOH, R and X having the same meanings as in the silica-based zinc compound according to one or more of claims 1 to 7, with a trialkyloxy silane or triaryloxy silane or mixed alkyl-aryloxy trisubstituted silane in the presence of a catalyst to yield a silicon-containing addition product;

B) Impregnating a silica carrier selected from the group consisting of ordered mesoporous silica and irregular amorphous narrow pore silica with a solution of the a silicon-containing addition product in a solvent to yield a silica-based carboxylic acid;

C) Ion-exchanging the silica-based carboxylic acid with a zinc salt to yield the silica-based zinc compound.

In yet another aspect, the invention is directed to a method of producing carbamate compounds, comprising the step of reacting an organic amine with a dialkyl carbonate in the presence of a silica-based zinc compound according to the invention.

A brief summary of various possible embodiments of the invention firstly follows:

In a first embodiment of the silica-based zinc compound according to the invention, which can be combined with all other embodiments, X is an aliphatic chain of 2 to 9 carbon atoms that optionally comprises ether moieties.

In a second embodiment of the silica-based zinc compound according to the invention, which is a particular variant of the first embodiment, X is selected from the group consisting of —$(CH_2)_2$—, —$(CH_2)_9$— and —$CH_2$—O—$(CH_2)_2$—.

In a third embodiment of the silica-based zinc compound according to the invention, which can be combined with all other embodiments, silica-based zinc compound (a) has a structure A in which the mono anion [Y] comprises a carboxylate group, the carboxylate oxygen atoms coordinating to the zinc atom and the carboxylate carbon atom being covalently connected to the silica carrier [$SiO_2$] via a chain of the same structure as $CH_2$—CHR—X, or (b) has a structure B in which the mono anion [Y] is not covalently connected to the [$SiO_2$] carrier, or (c) exists as a mixture of structures A and B.

In a fourth embodiment of the silica-based zinc compound according to the invention, which is a particular variant of the third embodiment, the mono anion of structure B is selected from the group consisting of chloride, bromide, iodide, acetate, naphthenate, octanoate, propionate, salicylate, pivalate, acrylate, p-chlorobenzoate, phenolate, formate, chloroacetate, acetylacetonate, oxalate, and trifluoroacetate.

In a fifth embodiment of the silica-based zinc compound according to the invention, which is a particular variant of the fourth embodiment, the mono anion of structure B is acetate.

In a sixth embodiment of the silica-based zinc compound according to the invention, which can be combined with all other embodiments, the ordered mesoporous silica is selected from the group consisting of SBA-1, SBA-2, SBA-3, SBA-6, SBA-8, SBA-11, SBA-12, SBA-15, SBA-16, MCM-41, MCM-48, and FSM-16, and the irregular amorphous narrow pore silica is a silica gel with an average pore diameter in the range of 2.5 nm to 7.5 nm, and particle sizes in the range of 35-500 μm.

In a particular embodiment of the method for producing a silica-based zinc compound according to the invention, the zinc salt is selected from the group consisting of zinc(II) chloride, bromide, iodide, acetate, naphthenate, octanoate, propionate, salicylate, pivalate, acrylate, p-chlorobenzoate, phenolate, formate, chloroacetate, acetylacetonate, oxalate, and trifluoroacetate. This embodiment can be combined with all embodiments of the silica-based zinc compound according to the invention with the proviso that silica-based zinc compounds comprising structure A require a zinc carboxylate.

In a first embodiment of the method for producing carbamate compounds according to the invention, the dialkyl carbonate is selected from the group consisting of propyl carbonate, ethyl carbonate, and methyl carbonate. This embodiment can be combined with all embodiments of the silica-based zinc compound according to the invention and with all embodiments of its preparation method.

In a second embodiment of the method for producing carbamate compounds according to the invention, the reaction of the organic amine with the dialkyl carbonate is carried out at a molar ratio of organic amine to Zn catalyst ranging from 10:1 to 20:1. This embodiment can be combined with all embodiments of the silica-based zinc compound according to the invention and with all embodiments of its preparation method.

In a third embodiment of the method for producing carbamate compounds according to the invention, the reaction of the organic amine with the dialkyl carbonate is carried out at a temperature ranging from 150° C. to 200° C. for a reaction time ranging from 0.5 h to 6 h. This embodiment can be combined with all embodiments of the silica-based zinc compound according to the invention and with all embodiments of its preparation method.

In a fourth embodiment of the method for producing carbamate compounds according to the invention, the organic amine is an aromatic amine selected from the group consisting of aniline, 2,4-diamino-N-phenylaniline, o-, m-, and p-phenylenediamine, 2,4-diaminotoluene, 2,6-diaminotoluene, 1,2,4,5-tetraaminobenzene, 4-methoxy-m-phenylenediamine, 4-amino-N-phenylaniline, 2-amino-N-methylaniline, N-isobutyl-p-phenyldiamine, o-, m-, and p-xylylenediamine, N-isoamyl-p-phenylenediamine, N-benzyl-p-phenylenediamine, N-cyclohexyl-p-diphenylenediamine, N,N'-di(n-propyl)-p-phenylenediamine, N-(n-butyl)-N'-benzyl-p-phenylenediamine, N,N'-dibenzyl-p-phenylenediamine, N-ethyl-m-phenylenediamine, N-ethyl-o-phenylenediamine, N-methyl-m-phenylenediamine, N,N'-diethyl-p-phenylenediamine, N-methyl-N-(n-propyl)-p-phenylenediamine, 4,4'-oxydianiline, 4,4'-ethylenedianiline, 2,4-bis(4-aminobenzyl)aniline, 4,4'-methylenebis(N,N-dimethylaniline); 4,4'-methylenebis(N-methylaniline); benzidine; N,N,N',N'-tetramethylbenzidine, bis(3,4-diaminophenyl)methane, bis(3-methyl-4-aminophenyl)methane, 2,2'-, 2,4'- or 4,4'-methylene dianiline, 1,6-hexamethylene diamine, isophorone diamine, (2-aminocylohexyl)-(4'-aminocylohexyl)-methane, bis-(4-aminocyclohexyl)-methane and mixtures of the aforementioned organic amines. This embodiment can be combined with all embodiments of the silica-based zinc compound according to the invention and with all embodiments of its preparation method.

In a fifth embodiment of the method for producing carbamate compounds according to the invention, which is a particular variant of the fourth embodiment, the organic amine is selected from the group consisting of aniline, 2,4-diaminotoluene, 2,6-diaminotoluene, and mixtures thereof or wherein the organic amine is selected from the group consisting of 2,2'-, 2,4'-, 4,4'-methylene dianiline, and mixtures thereof.

DETAILED DESCRIPTION

The invention will now be described in greater detail referring inter alia to the different embodiments described in short above. It is to be understood that different embodiments may be combined with each in any conceivable manner unless the technical context suggests otherwise.

In one preferred embodiment of the silica-based zinc compound of the invention, X is an aliphatic chain of preferably 2 to 9 carbon atoms that optionally comprises ether moieties. More preferred, X is selected from the group consisting of —(CH$_2$)$_2$—, —(CH$_2$)$_9$—, and —CH$_2$—O—(CH$_2$)$_2$—. Most preferred, X is —CH$_2$—O—(CH$_2$)$_2$—. In all embodiments of the silica-based zinc compound of the invention, it is preferred that R shall be hydrogen. Most preferred, X is —CH$_2$—O—(CH$_2$)$_2$— and [SiO$_2$] is irregular amorphous narrow pore silica.

Irrespective of the precise nature of the chain X, the catalyst of the invention preferably (a) has a structure A in which the mono anion [Y] comprises a carboxylate group, the carboxylate oxygen atoms coordinating to the zinc atom and the carboxylate carbon atom being covalently connected to the silica carrier [SiO$_2$] via a chain of the same structure as CH$_2$—CHR—X, or (b) has a structure B in which the mono anion [Y] is not covalently connected to the [SiO$_2$] carrier, or (c) exists as a mixture of structures A and B.

It is to be understood that the variants (a) and (b) are meant to describe alternatives, i.e. variant (a) excludes structure B (i.e. within the limits of analytical detection) and variant (b) excludes structure A (again within the limits of analytical detection). See the examples for a visualization of both structures. In variant (a), "within the limits of analytical detection" refers to the absence of free (i.e. not covalently connected to the [SiO$_2$] carrier) carboxylate anions (derived from the ZnY$_2$ precursor—see below for details—, which is a zinc carboxylate in variant (a)) as determined by ion chromatography (see examples for details) in the final catalyst. In variant (b), "within the limits of analytical detection" means that in the final catalyst all mono anions [Y] (which may or may not be carboxylate anions in variant (b)) are free mono anions as defined above, again as determined by ion chromatography (see examples for details).

In the variants (b) and (c), the mono anion [Y] in structure B is preferably selected from the group consisting of chloride, bromide, iodide, acetate, naphthenate, octanoate, propionate, salicylate, pivalate, acrylate, p-chlorobenzoate, phenolate, formate, chloroacetate, acetylacetonate, oxalate, and trifluoroacetate. Acetate is the most preferred mono anion [Y] in this embodiment. (The mono anion of structure B corresponds to the anion of the zinc salt used in Step C) of the preparation method; see below.)

As regards the silica carrier [SiO$_2$] in [SiO$_2$]—CH$_2$—CHR—X—COOZn[Y], the invention comprises two alternatives:

(1) The silica carrier is chosen from ordered mesoporous silica. In this alternative, SBA-1, SBA-2, SBA-3, SBA-6, SBA-8, SBA-11, SBA-12, SBA-15, SBA-16, MCM-41, MCM-48 or FSM-16 are preferred starting materials to be converted to the covalently bound [SiO$_2$] in the silica-based zinc compound, with mesostructured SBA-15 silica (2D hexagonal structure, channelled, particle size <150 μm) being a particularly suitable silica carrier starting material to be converted to the covalently bound [SiO$_2$] in the silica-based zinc compound. The terms "SBA" (Santa Barbara amorphous), "MCM" (Mobil composition of matter) and "FSM" (folded sheet material), including their respective denotations "-1", "-2" and the like, are well-known in the art. Reference is made to "Ordered Nanoporous Structure" (authors: Shen, J.; Chu, B.; Liu, Y.) in *Handbook of Nanophysics: Functional Materials*; Sattler, K. D., Ed.; CRC Press: Boca Raton, 2011; Vol. 5, chapter 10, especially pages 10-4, 10-8, and 10-9. In the context of this invention, all values for "particle size" are to be understood as referring to values as explained under no. III below.

(2) The silica carrier is chosen from irregular amorphous narrow pore silica. In this alternative, (in particular high-purity grade) silica gel with an average pore diameter in the range of 2.5 nm to 7.5 nm, such as silica gel 60 with an average pore diameter of 60 Å (6.0 nm), and particle sizes in the range of 35-500 μm is a preferred starting material to be converted to the covalently bound [SiO$_2$] in the silica-based zinc compound. More particularly, commercially available silica gel fractions having producer-specified particle sizes of 35-70 μm, 40-63 μm, 63-200 μm, 150-250 μm or 250-500 μm are preferred starting materials to be converted to the covalently bound [SiO$_2$] in the silica-based zinc compound, with silica gel 60 230-400 mesh ASTM having an average pore diameter of 6.7 nm, a specific surface area of 435 m$^2$/g, a pore volume of 0.73 mL/g, and a particle size of 40-63 μm being a particularly suitable silica carrier starting material to be converted to the covalently bound [SiO$_2$] in the silica-based zinc compound. In the context of this invention, all values for "pore volume" are to be understood as referring to values as determined by the Barrett-Joyner-Halenda (BJH) method as described in more detail later on in this description under no. II below. Particle sizes being in the range of 35-500 μm (or in any preferred range within these boundaries) means that all particles of other sizes have been removed within the limits of analytical detection (sieving analysis; see also below under no. III).

Silica carriers as described above are commercially available and/or can be prepared according to literature-known protocols. Preferred textural parameters as determined following the IUPAC technical report of 1994 (recommendations for characterization of porous solids, see *Pure Appl. Chem.* 1994, 66, 1739) by Brunauer-Emmett-Teller (BET) adsorption isotherm (for specific surface area; see also no. I below) and Barrett-Joyner-Halenda (BJH) method (for average pore diameter and pore volume) in N$_2$ are:

For silica carrier (1):

500 m$^2$/g<specific surface area<1000 m$^2$/g and 0.9 mL/g<pore volume<1.1 mL/g for silica carrier (1).

For silica carrier (2):

300 m$^2$/g<specific surface area<500 m$^2$/g and 0.5 mL/g<pore volume<0.8 mL/g for silica carrier (2).

Descriptions of the Applicable Measurement Methods are Provided in the Following:

I. Specific Surface Area:

Nitrogen isotherms at 77 K were measured on a Quantachrome Autosorb iQ analyzer. Prior to the analysis, the samples were degassed in vacuum at 120° C. for 12 h. The BET method was applied to calculate the specific surface area by using the calculations originally described by Brunauer, Emmett and Teller in J. Am. Chem. Soc. 1938, 60, 309.

II. Total Pore Volume and the Average Pore Diameter:

The desorption branch of the nitrogen isotherms determined as described under no. I were used to calculate the total pore volume and the average pore diameter by using the calculations described by Barrett, Joyner and Halenda in J. Am. Chem. Soc. 1951, 73, 373.

III. Particle Size Values:

Particle size values are regularly stated by the corresponding commercial source of the silica carrier. Usually, these values are reliable and can be referred to without limitation. In case of doubt, particle sizes as determined by dry sieve analysis as specified in DIN 66165 (version of April 1987), carried out with a vibratory sieving machine, are authoritative. Sieving can also be used to prepare fractions of silica carrier having a specific particle size range that is not commercially available.

The present invention is also directed towards a method for producing a catalyst compound according to the invention, comprising the steps of:

A) Reacting an unsaturated carboxylic acid of the formula $CH_2=CR-X-COOH$, wherein X and R have the meanings as described above, with a trialkyloxy silane or triaryloxy silane or mixed alkyl-aryloxy trisubstituted silane in the presence of a catalyst to yield the corresponding silicon-containing addition product;

B) Impregnating a silica carrier selected from the group consisting of ordered mesoporous silica and irregular amorphous narrow pore silica with a solution of the silicon-containing addition product in a solvent to yield a silica-based carboxylic acid;

C) Ion-exchanging the silica-based carboxylic acid with a zinc salt.

The invention is also directed to a silica-based zinc compound obtainable by the aforementioned method.

The addition Step A) can be described by the following equation:

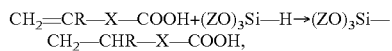
$$CH_2=CR-X-COOH+(ZO)_3Si-H \rightarrow (ZO)_3Si-CH_2-CHR-X-COOH,$$

wherein Z represents the alkyl and/or aryl residues of the alkyloxy, aryloxy or mixed alkyl-aryloxy silane. The residue Z is preferably selected from the group consisting of methyl, ethyl, and phenyl. The catalyst used in Step A) is preferably selected from the group consisting of $PtO_2$, $H_2PtCl_6$, $Pt(PPh_3)_4$, and Pt/C. As regards process conditions, Step A) is preferably carried out as follows:

Under an inert atmosphere, trisubstituted silane (1 equiv.) is added dropwise to a mixture of unsaturated carboxylic acid (1 equiv.) and catalyst (0.001 equiv.) in dry THF at 0° C. The mixture is stirred at 0° C. for 6 h followed by another 10 h at room temperature. Then, the mixture is filtered under an inert atmosphere and the filtrate evaporated in vacuo to give the corresponding silane carboxylic acid.

The solvent used in Step B) is preferably selected from the group consisting of toluene, benzene, cyclohexane, and hexane. The impregnation step B) can be described by the following equation and is preferably carried out as follows:

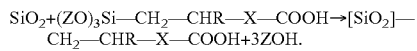
$$SiO_2+(ZO)_3Si-CH_2-CHR-X-COOH \rightarrow [SiO_2]-CH_2-CHR-X-COOH+3ZOH.$$

Previously dried (120° C. overnight) silica support $SiO_2$ is impregnated with a solution of the previously obtained silane carboxylic acid in dry toluene. The overall volume of the final solution is chosen such that it is equal to the total pore volume of the silica gel carrier used. The impregnation is carried out by slowly adding the silane carboxylic acid solution over the silica support while stirring vigorously with a vortex stirrer (3000 rpm). Once the addition is complete, the material is left at room temperature for 3 h and is then heated for 15 h at 120° C. in vacuo (10 mbar). The material is then sequentially washed with toluene, dichloromethane, hexane, and diethyl ether and dried for 3 h at 120° C. in vacuo (10 mbar).

It is to be understood that after completion of the impregnation step the silicon of the intermediate silicon-containing addition product $(ZO)_3Si-CH_2-CHR-X-COOH$ is considered an integral part of the silica carrier $[SiO_2]$ of the silica-based carboxylic acid. In the latter compound, the silica carrier is covalently bound to the terminal methylene group of "$CH_2-CHR-X-COOH$", this being indicated by the spelling $[SiO_2]$ in the context of this invention.

The zinc salt used in Step C) is preferably selected from the group consisting of zinc(II) chloride, bromide, iodide, acetate, naphthenate, octanoate, propionate, salicylate, pivalate, acrylate, p-chlorobenzoate, phenolate, formate, chloroacetate, acetylacetonate, oxalate, and trifluoroacetate (salts of the type $ZnY_2$, Y being the respective anion of the salt). The ion exchange step C) can be described by the following equation and is preferably carried out as follows:

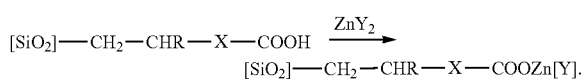
$$[SiO_2]-CH_2-CHR-X-COOH \xrightarrow{ZnY_2} [SiO_2]-CH_2-CHR-X-COOZn[Y].$$

[Y] represents the anion of the salt $ZnY_2$ in its state bound to "$[SiO_2]-CH_2-CHR-X-COOZn$". This bonding of [Y] involves ionic bonding to zinc. In certain embodiments of the invention, this bonding of [Y] may also involve covalent bonding to the carrier $[SiO_2]$ (see Scheme 1 for illustration). However, such covalent bonding does not necessarily occur in all embodiments of the invention. Whether or not covalent bonding of the type shown in Scheme 1 is involved depends on the nature of $ZnY_2$ and on the nature of the precursor $[SiO_2]-CH_2-CHR-X-COOH$. Thus, the designation [Y] indicates possible differences in the anion in its state bound to "$[SiO_2]-CH_2-CHR-X-COOZn^+$", but it also encompasses embodiments in which the anion in its state bound to "$[SiO_2]-CH_2-CHR-X-COOZn^+$" is identical to the anion $Y^-$ of $ZnY_2$.

The resulting carboxylic acid containing material is subjected to ion exchange employing aqueous zinc salt solutions. To a portion of the latter material, a zinc salt solution, for example a zinc acetate solution (0.4 M; 40 mL; 20 mL/g), is added, the mixture is then heated with stirring at 65° C. for 1 h, and the aqueous solution is filtered off and discarded. This process is repeated two more times with the zinc salt solution. The zinc-containing material is thoroughly washed with deionized water, filtered and dried for 3 h at 120° C. in vacuo (10 mbar).

Since the silicon of the intermediate silicon-containing addition product $(ZO)_3Si-CH_2-CHR-X-COOH$ is considered an integral part of the silica carrier of the silica-based carboxylic acid obtained in the impregnation step, it is also considered an integral part of the silica carrier $[SiO_2]$ of the silica-based zinc compound obtained in the ion exchange step, i.e. it is also considered an integral part of the silica carrier $[SiO_2]$ of the silica-based zinc compound of the invention.

A further aspect of the invention is a method of producing carbamate compounds, comprising the step of reacting an organic amine with a dialkyl carbonate in the presence of a catalyst, wherein the catalyst is the silica-based zinc compound of the invention as described above.

The dialkyl carbonate is preferably selected from the group consisting of propyl, ethyl, and methyl carbonate, the latter being particularly preferred.

The reaction of the organic amine with the dialkyl carbonate is preferably carried out at a molar ratio of organic amine to Zn catalyst ranging from 10:1 to 20:1.

As regards process conditions, the reaction of the organic amine with the dialkyl carbonate is carried out at a temperature ranging from 150° C. to 200° C. for a reaction time ranging from 0.5 h to 6 h, preferably at a temperature ranging from 180° C. to 190° C. for a reaction time ranging from 1 h to 4 h, a temperature ranging from 180° C. to 190° C. and a reaction time from 1.5 h to 2.5 h, in particular 2 h being most preferred. The reaction time refers to the time the reaction is allowed to proceed after the desired temperature has been reached.

The method according to this invention may for example use aliphatic, cycloaliphatic or aromatic amines or a mixture of two or more amine compounds as a starting material. The aromatic amine is a compound having at least one aromatic ring and at least one amino group bound to the aromatic ring. When the aromatic amine has more than one aromatic ring, the rings may be condensed or joined by at least one common ring member, a bond between a ring member of each aromatic ring or a divalent moiety. The divalent moiety preferably comprises C, O, S or N, more preferably from 1 to 6 C atoms. In a preferred embodiment, the divalent moiety is methylene.

At least one substituent of an aromatic amine is an amino group. Preferably at least two substituents, preferably up to four substituents, and even more preferably two substituents, are amino groups. The amino groups are preferably primary or secondary amino groups, and more preferably primary amino groups. Preferably, at least one amino group is in the 2-, 4- or 6-position, more preferably at least one amino group is in the 2-position, relative to a purely C,H-substituent, preferably a methyl group, substituent on at least one, preferably only one, aromatic ring. More preferably, amino groups are present in the 2- and the 4- or 6-position of at least one, preferably only one, aromatic ring.

In general, examples for aromatic amines include:

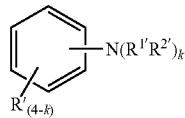

wherein R' is hydrogen, halogen, linear or branched C1-C12 alkyl, linear or branched C1-C12 alkoxy, linear or branched C1-C12 alkoxyalkyl, or C1-C12 alkylamino; $R^{1'}$ and $R^{2'}$ are independently hydrogen, or linear or branched C1-C12 alkyl; k is an integer 2-4.

Other examples include:

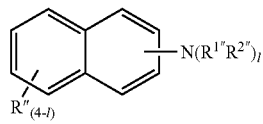

wherein R" is hydrogen, halogen, linear or branched C1-C12 alkyl, linear or branched C1-C12 alkoxy, linear or branched C1-C12 alkoxyalkyl, or C1-C12 alkylamino; $R^{1''}$ and $R^{2''}$ are independently hydrogen, or linear or branched C1-C12 alkyl; l is an integer 2-4; and the substituents R" and $NR^{1''}R^{2''}$ can be present at any position of the naphthalene ring.

Further examples include:

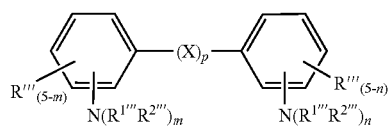

wherein R''' is hydrogen, halogen, linear or branched C1-C12 alkyl, linear or branched C1-C12 alkoxy, linear or branched C1-C12 alkoxyalkyl, or C1-C12 alkylamino; $R^{1'''}$ and $R^{2'''}$ are independently hydrogen, or linear or branched C1-C12 alkyl; X is linear or branched C1-C6 alkylene, O, S, NR'''; m and n is 0 or an integer 1-3 and m+n≥2; and p is 0 or 1.

In another embodiment of this method the organic amine is an aromatic amine selected from the group of 2,4-diamino-m-phenylaniline, o-, m-, and p-phenylenediamine, 2,4-diaminotoluene, 2,6-diaminotoluene, 1,2,4,5-tetraaminobenzene, 4-methoxy-m-phenylenediamine, 4-amino-N-phenylaniline, 2-amino-N-methylaniline, N-isobutyl-p-phenyldiamine, o-, m-, and p-xylylenediamine, N-isoamyl-p-phenylenediamine, N-benzyl-p-phenylenediamine, N-cyclohexyl-p-diphenylenediamine, N,N'-di(n-propyl)-p-phenylenediamine, N-(n-butyl)-N'-benzyl-p-phenylenediamine, N,N'-dibenzyl-p-phenylenediamine, N-ethyl-m-phenylenediamine, N-ethyl-o-phenylenediamine, N-methyl-m-phenylenediamine, N,N'-diethyl-p-phenylenediamine, N-methyl-N-(n-propyl)-p-phenylenediamine, 4,4'-oxydianiline, 4,4'-ethylenedianiline, 2,4-bis(4-aminobenzyl)aniline, 4,4'-methylenebis(N,N-dimethylaniline); 4,4'-methylenebis (N-methylaniline); benzidine; N,N,N',N'-tetramethylbenzidine, bis(3,4-diaminophenyl)methane, bis(3-methyl-4-aminophenyl)methane, 2,2'-, 2,4'- or 4,4'-methylene dianiline, 1,6-hexamethylene diamine, isophorone diamine, (2-aminocylohexyl)-(4'-aminocyclohexyl)-methane and/or bis-(4-aminocyclohexyl)-methane.

In a particularly preferred embodiment of this method the amine is selected from 2,4-diaminotoluene, 2,6-diaminotoluene, and mixtures thereof. Most preferred is a technical mixture such as 80% 2,4-diaminotoluene and 20% 2,6-diaminotoluene.

In another preferred embodiment of this method the amine is selected from 2,2'-, 2,4'-, 4,4'-methylene dianiline, and mixtures thereof.

An advantage of the method for producing carbamates according to the invention is the reusability of the catalyst. The silica-based zinc compound of the invention that is used as catalyst can be removed from the reaction mixture (preferably by filtration), washed (preferably with the same solvent as used for the alkoxycarbonylation reaction, i.e. dimethyl carbonate, followed by acetone), dried (preferably at a temperature ranging from 100° C. to 150° C. and a pressure ranging from 0.001 bar$_{(abs.)}$ to 1.00 bar$_{(abs)}$). Reusing the catalyst in this way is particularly preferred for catalysts in which the chain X comprises ether moieties, more particularly preferred for X=—CH$_2$—O—(CH$_2$)$_2$—, and most preferred for X=—CH$_2$—O—(CH$_2$)$_2$— and [SiO$_2$]=irregular amorphous narrow pore silica.

The present invention will now be described with reference to the following examples without wishing to be limited thereto.

EXAMPLES

A. Preparation of Silica-Based Zinc Compounds

Example A.1: Preparation of Irregular Amorphous Narrow Pore [SiO$_2$]—(CH$_2$)$_3$—O—(CH$_2$)$_2$—COOZn[Y]

Under an inert atmosphere, triethoxysilane (3.39 g, 97%, 20.0 mmol) was added dropwise to a mixture of 3-allyloxypropionic acid (2.74 g, 95%, 20.0 mmol), dry THF (3.0 mL) and PtO$_2$ (4.6 mg, 0.02 mmol) at 0° C. The mixture was stirred at 0° C. for 6 h followed by another 10 h at RT. After the reaction was complete, the mixture was filtered through a PTFE syringe filter and the filtrate evaporated in vacuo to give the corresponding alkoxy silane carboxylic acid (5.83 g). A minor by-product, whose structure was determined to be the corresponding cyclic ester by $^1$H-NMR analysis, was also observed (16%). This reaction mixture was used without any further purification.

$^1$H NMR: δ 11.26 (s, 1H), 3.67 (q, 6H, J=7.0 Hz), 3.59-3.51 (m, 2H), 3.33-3.24 (m, 2H), 2.49-2.42 (m, 2H), 1.61-1.46 (m, 2H), 1.07 (t, 9H, J=7.0 Hz), 0.55-0.42 (m, 2H) ppm; $^{13}$C{$^1$H}NMR: δ 176.3, 73.1, 65.5, 58.2, 34.6, 22.6, 18.0, 6.2 ppm; $^{29}$Si{$^1$H} NMR: δ −49.4 ppm.

Then, 4.40 g of silica gel (irregular amorphous narrow pore, 40-63 μm particle size, pore volume: 0.73 mL/g, 435 m$^2$/g, average pore diameter 6.7 nm, Merck) previously dried (120° C. overnight) were impregnated with a solution of the previously obtained 3-(3-(triethoxysilyl)propoxy)propanoic acid (1.94 g, 84%, 5.57 mmol) and dry toluene (ca. 2 mL toluene; the overall volume of the final solution was 3.2 mL). The impregnation was carried out by slowly adding the alkoxy silane carboxylic acid solution over the silica support while stirring vigorously with a vortex stirrer (3000 rpm). Once the addition was complete, the material was left at RT for 3 h and then heated for 15 h at 120° C. in vacuo (10 mbar). The material was then sequentially washed with toluene, dichloromethane, hexane, and diethyl ether (20 mL each) and dried for 3 h at 120° C. in vacuo (10 mbar) to yield 5.68 g of a white powder.

The resulting carboxylic acid containing material was subjected to ion exchange employing aqueous zinc acetate solutions. To a portion of 2.0 g of the latter material, a zinc acetate solution (0.4 M; 40 mL; 20 mL/g) was added, the mixture was then heated with stirring at 65° C. for 1 h and the aqueous solution was filtered off and discarded. This process was repeated two more times with a zinc acetate solution, as that indicated above. The zinc-containing material was thoroughly washed with deionized water (8×50 mL), filtered and dried for 3 h at 120° C. in vacuo (10 mbar) to yield 1.8 g of a white powder corresponding to the [SiO$_2$]—(CH$_2$)$_3$—O—(CH$_2$)$_2$—COOZn[Y]_material, whose zinc content was determined to be 0.78 mmol [Zn]/g, (complexometric titration with EDTA).

Characterization Data of [SiO$_2$]—(CH$_2$)$_3$—O—(CH$_2$)$_2$—COOZn[Y]

TGA (air, 30-550° C., 5° C./min): mass loss at 80° C. (2.62%) and 270° C. (9.14%); XRPD (2 θ range 5°-70°): no diffraction peaks observed; BET surface area analysis (N$_2$ adsorption-desorption isotherm): 0.46 mL/g total pore volume, 290 m$^2$/g specific surface area; complexometric titration: 0.78 mmol [Zn]/g; ion chromatography: 0.014 mmol ACO$^-$ groups/g (<2% of ACO$^-$ groups with respect to [Zn] present in the modified SiO$_2$); $^{13}$C CP-MAS NMR: δ 182.1, 73.1, 67.2, 37.0, 23.0, 8.6 ppm; $^{29}$Si CP-MAS NMR: δ −51.2, −59.4, −68.3, −94.1, −104.0, −113.3 ppm; FT-IR (ATR, solid, $\bar{v}$/cm$^{-1}$): 2945 (out-of-phase stretch CH$_2$), 2882 (in-phase stretch CH$_2$), 1568 (asym. stretch COO), 1445 (deformation CH$_2$), 1420 (sym. stretch COO), 1054 (asym. stretch Si—O—Si); zinc content: 0.78 mmol [Zn]/g.

Repetitions of the reactions described above yielded products with the same spectroscopic and analytical data and with the following zinc contents:

Batch #2: 0.75 mmol [Zn]/g
Batch #3: 0.79 mmol [Zn]/g
Average value: 0.77 mmol [Zn]/g; standard deviation: 0.02 mmol [Zn]/g.

The analytical data (ion exchange) available for [SiO$_2$]—(CH$_2$)$_3$—O—(CH$_2$)$_2$—COOZn[Y] indicates predominantly (98 mass percent, based on the total mass of the silica-based zinc compound) a structure of type A, i.e. a structure in which the mono anion [Y] comprises a carboxylate group, the carboxylate oxygen atoms coordinating to the zinc atom and the carboxylate carbon atom being covalently connected to the silica carrier [SiO$_2$] via a chain of the same structure as CH$_2$—CHR—X. A minor amount (2 mass percent, based on the total mass of the silica-based zinc compound) exists in structure of type B, the mono anion [Y] being acetate (the counter ion of the zinc salt used in the ion exchange step). Thus, the catalyst [SiO$_2$]—(CH$_2$)$_3$—O—(CH$_2$)$_2$—COOZn[Y] when prepared as described above is of variant (c). The predominant structure of type A may be visualized as follows:

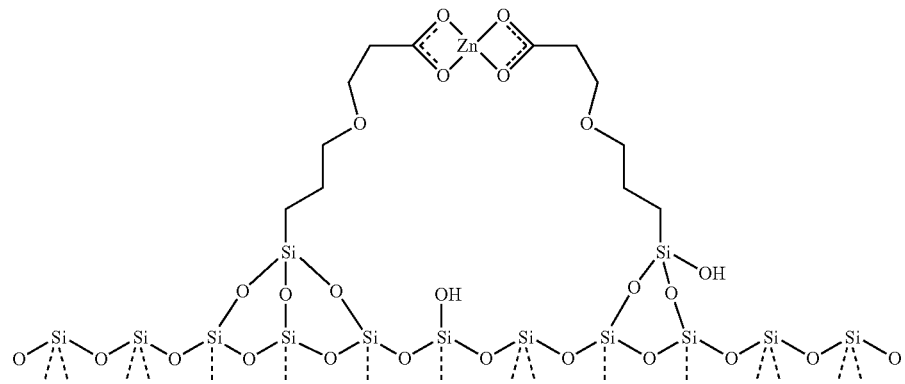

Scheme 1: Possible structure of type A of [SiO$_2$]—(CH$_2$)$_3$—O—(CH$_2$)$_2$—COOZn[Y] catalyst. It should be noted that the extract of the structure of the silica carrier [SiO$_2$] shown here is not to be understood as limiting. Deviations therefrom are possible.

The less dominant structure of type B may be visualized as follows:

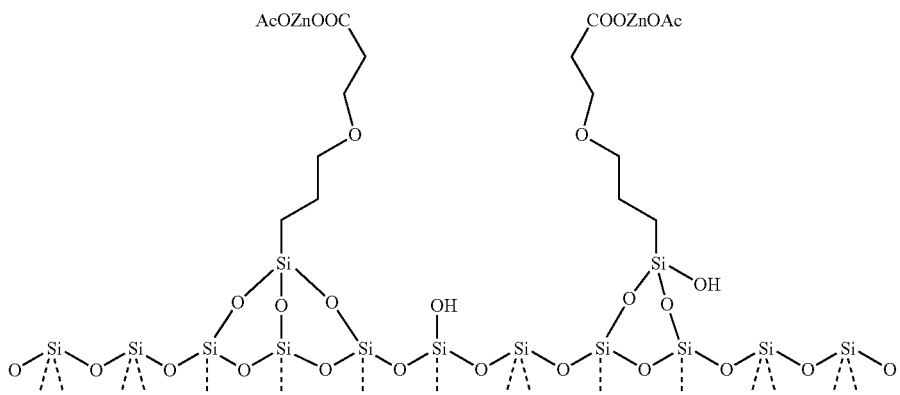

Scheme 2: Possible structure of type B of [SiO₂]—(CH₂)₃—O—(CH₂)₂—COOZn[Y] catalyst. It should be noted that the extract of the structure of the silica carrier [SiO₂] shown here is not to be understood as limiting. Deviations therefrom are possible.

Example A.2: Preparation of Irregular Amorphous Narrow Pore [SiO₁]—(CH₂)₄—COOZn[Y]

5-(Triethoxysilyl)pentanoic acid was prepared following the same experimental protocol as that described above for Example 1, with the following amounts of reagents: triethoxysilane (4.32 g, 97%, 25.0 mmol), pent-4-enoic acid (2.50 g, 25.0 mmol), dry THF (3.0 mL) and PtO₂ (5.7 mg, 0.025 mmol).

Along with the desired compound, the corresponding cyclic ester was also observed as a minor by-product (4%). The alkoxy silane carboxylic acid was obtained as an oil (6.44 g, 96%, 23.4 mmol, 94% yield) and used without any further purification.

$^1$H NMR: δ 11.34 (s, 1H), 3.72 (q, 6H, J=7.0 Hz), 2.29-2.20 (m, 2H), 1.64-1.52 (m, 2H), 1.45-1.32 (m, 2H), 1.12 (t, 9H, J=7.0 Hz), 0.61-0.49 (m, 2H) ppm; $^{13}$C{$^1$H} NMR: δ 179.5, 58.2, 33.6, 27.8, 22.2, 18.1, 10.0 ppm; $^{29}$Si{$^1$H} NMR: δ −45.4 ppm.

5-(Triethoxysilyl)pentanoic acid was attached to SiO₂ following the same experimental protocol as that described for Example 1, with the following amounts of reagents: Silica gel (4.09 g, irregular amorphous narrow pore, 40-63 μm particle size, pore volume: 0.73 mL/g, 435 m²/g, average pore diameter 6.7 nm, Merck) previously dried (120° C. overnight), 5-(trimethoxysilyl)pentanoic acid (2.00 g, 96%, 7.25 mmol) and dry toluene (ca. 1.7 mL toluene; the overall volume of the final solution was 3.0 mL). The COOH-containing silica gel was obtained as a white powder (5.19 g).

The resulting carboxylic acid containing material was subjected to ion exchange following the same experimental protocol as that described for [SiO₂]—(CH₂)₃—O—(CH₂)₂—COOZn[Y], with the following amounts of reagents: COOH-containing silica gel (1.5 g) and aqueous zinc acetate (0.4 M; 30 mL; 20 mL/g). [SiO₂]—(CH₂)₄—COOZn[Y] was obtained as a white powder (1.4 g).

Characterization Data for [SiO₂]—(CH₂)₄—COOZn[Y]

TGA (air, 30-550° C., 5° C./min): mass loss at 80° C. (2.36%) and 460° C. (9.35%); XRPD (2 θ range 5°-70°): no diffraction peaks observed; BET surface area analysis (N₂ adsorption-desorption isotherm): 0.43 mL/g total pore volume, 282 m²/g specific surface area; complexometry: 1.00 mmol [Zn]/g, ion chromatography: 0.016 mmol ACO⁻ groups/g (<2% of ACO⁻ groups with respect to [Zn] present in the modified SiO₂); FT-IR (ATR, solid, ν̄/cm⁻¹): 2936 (out-of-phase stretch CH₂), 2877 (in-phase stretch CH₂), 1557 (asym. stretch COO), 1454 (deformation CH₂), 1423 (sym. stretch COO), 1052 (asym. stretch Si—O—Si); zinc content: 1.00 mmol [Zn]/g.

Example A.3: Preparation of Ordered Mesoporous [SiO₂]—(CH₂)₄—COOZn[Y]

Previously obtained 5-(triethoxysilyl)pentanoic acid was attached to ordered mesoporous silica SBA15 following the same experimental protocol as that described for Example 1, with the following amounts of reagents: SBA15 silica gel (2.10 g, mesostructured [average pore diameter 5.8 nm,], pore volume: 0.94 mL/g, 656 m²/g, Aldrich) previously dried (120° C. overnight), 5-(trimethoxysilyl)pentanoic acid (1.26 g, 96%, 4.57 mmol) and dry toluene (ca. 1.0 mL toluene; the overall volume of the final solution was 1.9 mL). The COOH-containing silica gel was obtained as a white powder (2.65 g).

The resulting carboxylic acid containing material was subjected to ion exchange following the same experimental protocol as that described for [SiO₂]—(CH₂)₃—O—(CH₂)₂—COOZn[Y], with the following amounts of reagents: COOH-containing silica gel (1.5 g) and aqueous zinc acetate (0.4 M; 30 mL; 20 mL/g). Ordered mesoporous [SiO₂]—(CH₂)₄—COOZn[Y] was obtained as a white powder (1.4 g).

Characterization Data for Ordered Mesoporous [SiO₂]—(CH₂)₄—COOZn[Y]

TGA (air, 30-550° C., 5° C./min): mass loss at 80° C. (2.67%) and 460° C. (10.32%); XRPD (2 θ range 5°-70°): no diffraction peaks observed; BET surface area analysis (N₂ adsorption-desorption isotherm): 0.56 mL/g total pore volume, 350 m²/g specific surface area; complexometric titration: 1.25 mmol [Zn]/g, ion chromatography: 0.015 mmol ACO⁻ groups/g (<2% of ACO⁻ groups with respect to [Zn] present in the modified SiO₂); FT-IR (ATR, solid, ν̄/cm⁻¹): 2935 (out-of-phase stretch CH₂), 2868 (in-phase stretch CH₂), 1557 (asym. stretch COO), 1457 (deformation CH₂), 1423 (sym. stretch COO), 1056 (asym. stretch Si—O—Si); zinc content: 1.25 mmol [Zn]/g.

Example A.4: Preparation of Irregular Amorphous Narrow Pore [SiO$_2$](CH$_2$)$_{11}$—COOZn[Y]

12-(Triethoxysilyl)dodecanoic acid was prepared following the same experimental protocol as that described above for Example 1, with the following amounts of reagents: triethoxysilane (2.56 g, 97%, 15.1 mmol), dodec-11-enoic acid (3.00 g, 15.1 mmol), dry THF (3.0 mL) and PtO$_2$ (3.4 mg, 0.015 mmol). Along with the desired compound, the corresponding cyclic ester was also observed as a minor by-product (12%). The alkoxy silane carboxylic acid was obtained as an oil (5.32 g, 88%, 12.9 mmol, 86% yield) and used without any further purification.

$^1$H NMR: δ 11.54 (s, 1H), 3.71 (q, 6H, J=7.0 Hz), 2.26-2.18 (m, 2H), 1.57-1.46 (m, 2H), 1.36-1.26 (m, 2H), 1.26-1.14 (m, 14H), 1.11 (t, 9H, J=7.0 Hz), 0.56-0.47 (m, 2H) ppm; $^{13}$C{$^1$H} NMR: δ 179.4, 58.1, 33.9, 33.0, 29.4, 29.4, 29.3, 29.1, 29.1, 28.9, 22.6, 22.6, 18.1, 10.2 ppm; $^{29}$Si{$^1$H} NMR: δ −44.7 ppm.

12-(Triethoxysilyl)dodecanoic acid was attached to SiO$_2$ following the same experimental protocol as that described for Example 1, with the following amounts of reagents: Silica gel (3.40 g, irregular amorphous narrow pore, 40-63 µm particle size, pore volume: 0.73 mL/g, 435 m$^2$/g, average pore diameter 6.7 nm, Merck) previously dried (120° C. overnight), 12-(triethoxysilyl)dodecanoic acid (1.48 g, 88%, 3.57 mmol) and dry toluene (ca. 1.6 mL toluene; the overall volume of the final solution was 2.5 mL). The COOH-containing silica gel was obtained as a white powder (4.12 g).

The resulting carboxylic acid containing material was subjected to ion exchange following the same experimental protocol as that described for [SiO$_2$]—(CH$_2$)$_3$—O—(CH$_2$)$_2$—COOZn[Y], with the following amounts of reagents: COOH-containing silica gel (2.0 g) and aqueous zinc acetate (0.4 M; 40 mL; 20 mL/g). [SiO$_2$]—(CH$_2$)$_{11}$—COOZn[Y] was obtained as a white powder (1.9 g).

Characterization Data for [SiO$_2$]—(CH$_2$)$_{11}$—COOZn[Y]

TGA (air, 30-550° C., 5° C./min): mass loss at 80° C. (2.05%) and 430° C. (16.36%); XRPD (2 θ range 5°-70°): no diffraction peaks observed; BET surface area analysis (N$_2$ adsorption-desorption isotherm): 0.30 mL/g total pore volume, 268 m$^2$/g specific surface area; complexometric titration: 0.81 mmol [Zn]/g, ion chromatography: 0.015 mmol ACO$^-$ groups/g (<2% of ACO$^-$ groups with respect to [Zn] present in the modified SiO$_2$); FT-IR (ATR, solid, $\bar{v}$/cm$^{-1}$): 2925 (out-of-phase stretch CH$_2$), 2854 (in-phase stretch CH$_2$), 1557 (asym. stretch COO), 1456 (deformation CH$_2$), 1418 (sym. stretch COO), 1054 (asym. stretch Si—O—Si); zinc content: 0.81 mmol [Zn]/g.

Example A.5: Preparation of a Siliceous Catalyst without Zinc Groups (Comparison)

With the aim of assessing the methoxycarbonylation background reaction mediated by the solid support (a siliceous material), (MeO)$_3$SiMe was grafted to irregular amorphous narrow pore silica gel following an identical procedure to that employed for covalently linking COOZn groups to the inorganic supports (see Example 1). Thus, a modified silica gel (SG-Me) was prepared by grafting identical amounts of (MeO)$_3$SiMe. The work-up and purification procedures employed were also the same than those employed for preparing the real catalysts. It should be noted that this material (SG-Me) is based on the same siliceous support and has the same functionalization degree as the real catalysts (with irregular amorphous narrow pore silica carriers), however it lacks zinc groups.

B. Alkoxycarbonylations of Aromatic Amines

General Procedure

The catalytic results presented below are based on a series of experiments employing the four different heterogeneous catalysts that have been prepared according to Examples A.1 to A.4 and the comparison catalyst prepared according to Example A.S. Catalytic assays were at least duplicated (a minimum of two reactions per catalyst and substrate were performed). Furthermore, two samples for HPLC quantitative analysis were made up for each reaction mixture and were analysed with the corresponding quantitative HPLC analytical method. The aromatic amines used as substrates were aniline, MDA and 2,4-TDA, as shown in the following scheme:

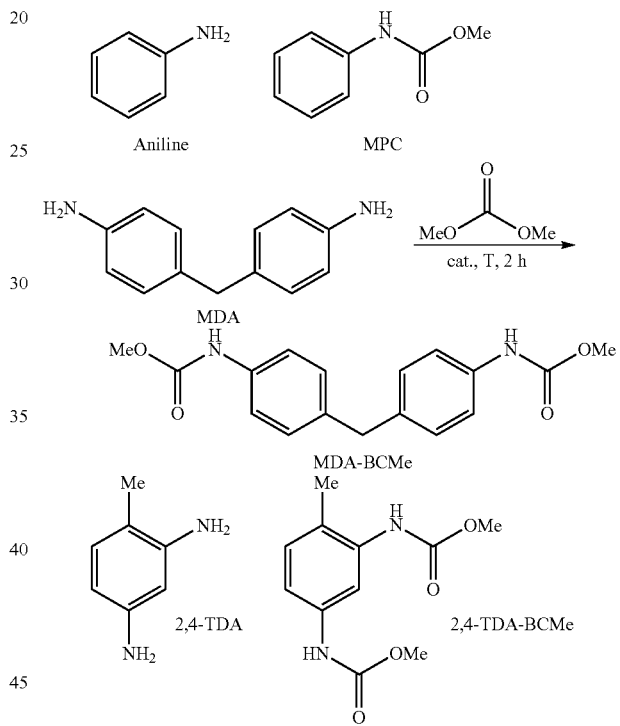

Crude product mixtures derived from the methoxycarbonylation reaction of aniline were analyzed by NMR using internal standards whereas crude product mixtures derived from the methoxycarbonylation reaction of MDA and TDA were analyzed by quantitative HPLC analysis using calibration curves. The analytical conditions for MDA and 2,4-TDA derivatives were as follows:

MDA-derivatives: Kromasil 100 C18 5 µm 4.6×150 column, RT, 1.0 mL/min, Injection=5 µL, UV detection 254 nm, Eluent A:100 mL CH$_3$CN, 900 mL H$_2$O, 0.01M NH$_4$Ac. Eluent B: 900 mL CH$_3$CN, 100 mL H$_2$O, 0.01M NH$_4$Ac. Gradient: 0 min 60% A, 40% B; 15 min 60% A, 40% B; 25 min 100% B; 30 min Stop. Retention times: Rt(MDA)=4.1 min, Rt(MDA-MCMe)=6.4 min, Rt(MDA-MMe)=8.4 min, Rt(MDA-BCMe)=10.0 min, Rt(MDA-BMe)=19.0 min.

2,4-TDA-derivatives: Kromasil 100 C18 5 µm 4.6×150, RT, 1.0 mL/min, Injection=5 µL, UV detection 225 nm, Eluent A:100 mL CH$_3$CN, 900 mL H$_2$O, 0.01M NH$_4$Ac. Eluent B: 900 mL CH$_3$CN, 100 mL H$_2$O, 0.01M NH$_4$Ac. Gradient: 0 min 100% A, 22 min 100% A; 48 min 80% A, 20% B; 60 min 55% A, 45% B; 80 min Stop. Retention times: Rt(2,4-TDA)=7.5 min, Rt(2,4-TDA-M-oMe)=15.0 min, Rt(2,4-TDA-M-pMe)=20.0 min, Rt(2,4-TDA-MC-oMe)=22.4 min, Rt(2,4-TDA-MC-pMe)=30.8 min, Rt(2,4-TDA-BMe)=42.0 min, Rt(2,4-TDA-BCMe)=45.1 min.

The reaction conditions that were used in the catalytic studies were based on the ones disclosed in WO 2014/187756 A1 (Example 2 in page 12, line 12), with the exception of the catalyst loading employed. The reaction conditions for each substrate are indicated below and catalyst loadings are expressed in molar ratio of dimethyl carbonate (DMC), amine and catalyst (based in [Zn] content).

Aniline: molar ratio DMC:amine:catalyst=25:1:0.05, T=180° C.

MDA: molar ratio DMC:amine:catalyst=25:1:0.05, T=180° C.

2,4-TDA: molar ratio DMC:amine:catalyst=30:1:0.10, T=190° C.

In order to recover and reuse the catalysts after the alkoxycarbonylation reactions, the crude reaction mixtures were filtered. The recovered heterogeneous catalysts were washed with acetone, and the solid residue was dried at 120° C. prior to its reuse. The results are indicated in each case and are labelled as cycle #2 in the Tables that summarise the results on catalysis in Examples B.2 to B.6 below. In the methoxycarbonylation of MDA, considerable amounts of insoluble and non-analysable materials were formed. The catalysts were separated from the reaction mixture together with these MDA-derived insoluble compounds, which could not be separated from the catalyst during the catalyst recycling process. Thus, catalytic studies with recycled catalyst implied adding these impurities to the reaction mixture.

Examples B.1 and B.2 (Comparisons): Catalyst From Example A.5 and No Catalyst, Respectively The results are summarised in Table 1.

TABLE 1

Methoxycarbonylation reactions using a blank catalyst (SG-Me, Example A.5) or no catalyst.

| Ex. | Reaction conditions | Substrate | Conversion (%) (SD) | High. Poss. Yield (%) (SD) [a] | Yield (%) (SD) [b] |
|---|---|---|---|---|---|
| B.1 | 190° C., 2 h, DMC, SG-Me as catalyst | 2,4-TDA | 73 | 8 | <1 |
| B.2 | 190° C., 2 h, DMC No catalyst | 2,4-TDA | 73 | 5 | 1 |

[a] Highest possible yield. Sum of the yield of the target biscarbamate and its intermediates.
[b] Yield of the desired biscarbamate.

Example B.3: Irregular Amorphous Narrow Pore [SiO$_2$]—(CH$_2$)$_4$—COOZn[Y] (of Example A.2) as Catalyst Table 2 summarises the results.

TABLE 2

Methoxycarbonylation reactions using irregular amorphous narrow pore [SiO$_2$]—(CH$_2$)$_4$—COOZn[Y] as the catalyst.[a]

| Ex. B.3.- | Substrate | Cycle | Conversion (%) (SD) | High. Poss. Yield (%) (SD) [b] | Yield (%) (SD) [c] | Alk. Amines (%)/Alk. Carb. (Σ area %)[d] |
|---|---|---|---|---|---|---|
| 1 | Aniline | #1 | >99 (0) | 95 (0) | 95 (0) | 4/2 |
| 2 | Aniline | #2 | >99 (0) | 98 (0) | 98 (0) | 2/0 |
| 3 | MDA | #1 | >99 (0) | 57 (2) | 42 (3) | 4/29 |
| 4 | MDA | #2 | 97 (2) | 54 (7) | 32 (11) | 7/23 |
| 5 | 2,4-TDA | #1 | >99 (0) | 46 (1) | 33 (2) | 4/32 |
| 6 | 2,4-TDA | #2 | >99 (1) | 36 (1) | 11 (2) | 18/28 |

[a] Values expressed as an average of all independent runs. Standard deviations are indicated in brackets.
[b] Highest possible yield: sum of the yield of the target carbamate and its precursors (i.e. the corresponding monocarbamates).
[c] Yield of the desired carbamate.
[d] Sum of areas of alkylated carbamates.

In comparison, the wide-pore supported catalyst described in *Catal. Sci. Technol.* 2015, 5, 109 and CN 102872912 A is said to give yields with aniline as reactant of up to 91.6%.

Example B.4: Ordered Mesoporous [SiO$_2$]—(CH$_2$)$_4$ COOZn[Y] (of Example A.3) as Catalyst Table 3 summarises the results.

TABLE 3

Methoxycarbonylation reactions using ordered mesoporous [SiO$_2$]—(CH$_2$)$_4$ COOZn[Y] as the catalyst.[a]

| Ex. B.4.- | Substrate | Cycle | Conversion (%) (SD) | High. Poss. Yield (%) (SD) [b] | Yield (%) (SD) [c] | Alk. Amines (%)/Alk. Carb. (Σ area %)[d] |
|---|---|---|---|---|---|---|
| 1 | Aniline | #1 | >99 (0) | 94 (0) | 94 (0) | 4/2 |
| 2 | Aniline | #2 | >99 (0) | 97 (0) | 97 (0) | 3/1 |
| 3 | MDA | #1 | 99 (1) | 54 (2) | 34 (6) | 6/26 |
| 4 | MDA | #2 | 97 (2) | 47 (5) | 23 (1) | 8/22 |
| 5 | 2,4-TDA | #1 | >99 (0) | 43 (1) | 28 (1) | 5/40 |
| 6 | 2,4-TDA | #2 | 96 (1) | 38 (6) | 12 (4) | 17/31 |

[a] Values expressed as an average of all independent runs. Standard deviations are indicated in brackets.
[b] Highest possible yield: sum of the yield of the target carbamate and its precursors (i.e. the corresponding monocarbamates).
[c] Yield of the desired carbamate.
[d] Sum of areas of alkylated carbamates.

Example B.5: Irregular Amorphous Narrow Pore [SiO$_2$]—(CH$_2$)$_{11}$COOZn[Y] (of Example A.4) as Catalyst Table 4 summarises the results.

TABLE 4

Methoxycarbonylation reactions using irregular amorphous narrow pore [SiO$_2$]—(CH$_2$)$_4$—COOZn[Y] as the catalyst.[a]

| Ex. B.5.- | Substrate | Cycle | Conversion (%) (SD) | High. Poss. Yield (%) (SD) [b] | Yield (%) (SD) [c] | Aik. Amines (%)/ Aik. Carb. (Σ area %)[d] |
|---|---|---|---|---|---|---|
| 1 | Aniline | #1 | >99 (0) | 93 (0) | 93 (0) | 4/4 |
| 2 | Aniline | #2 | >99 (0) | 98 (0) | 98 (0) | 1/1 |
| 3 | MDA | #1 | 98 (0) | 57 (0) | 34 (1) | 6/23 |
| 4 | MDA | #2 | 97 (2) | 50 (2) | 27 (6) | 7/21 |
| 5 | 2,4-TDA | #1 | 65 (1) | 3 (1) | <1 (0) | 45/10 |
| 6 | 2,4-TDA | #2 | | | | —/— |

[a]Values expressed as an average of all independent runs. Standard deviations are indicated in brackets.
[b] Highest possible yield: sum of the yield of the target carbamate and its precursors (i.e. the corresponding monocarbamates).
[c] Yield of the desired carbamate.
[d]Sum of areas of alkylated carbamates.

Example B.6: Irregular Amorphous Narrow Pore [SiO$_2$]—(CH$_2$)$_3$—O—(CH$_2$)$_2$—COOZn[Y] (of Example A.1) as Catalyst Table 5 summarises the results.

TABLE 5

Methoxycarbonylation reactions using irregular amorphous narrow pore [SiO$_2$]—(CH$_2$)$_3$—O—(CH$_2$)$_2$—COOZn[Y] as the catalyst.[a]

| Ex. B.6.- | Substrate | Cycle | Conversion (%) (SD) | High. Poss. Yield (%) (SD) [b] | Yield (%) (SD) [c] | Aik. Amines (%)/ Aik. Carb. (Σ area %)[d] |
|---|---|---|---|---|---|---|
| 1 | Aniline | #1 | >99 (0) | 93 (0) | 93 (0) | 6/2 |
| 2 | Aniline | #2 | >99 (0) | 97 (0) | 97 (0) | 2/1 |
| 3 | MDA | #1 | 99 (0) | 56 (3) | 40 (4) | 4/28 |
| 4 | MDA | #2 | >99 (0) | 68 (5) | 57 (5) | 2/24 |
| 5 | 2,4-TDA | #1 | >99 (0) | 46 (2) | 37 (1) | 3/39 |
| 6 | 2,4-TDA | #2 | >99 (0) | 67 (1) | 55 (2) | 1/26 |

[a]Values expressed as an average of all independent runs. Standard deviations are indicated in brackets.
[b] Highest possible yield: sum of the yield of the target carbamate and its precursors (i.e. the corresponding monocarbamates).
[c] Yield of the desired carbamate.
[d]Sum of areas of alkylated carbamates.

Recycled catalyst of Example A.1 mediated the methoxycarbonylation of 2,4-TDA with higher selectivity, reaching 55% and 67% yield of the desired biscarbamate and biscarbamate plus intermediates (i.e. 2- and 4-monocarbamates derived from 2,4-TDA; compare Examples B.6.5 and B.6.6 in Table 5). Despite containing MDA-derived impurities, recycled catalyst of Example A.1 gave slightly better results in the second cycle (for instance, yield in the desired biscarbamate increased from 40% in the first cycle to 57% in the second; compare entries B.6.3 and B.6.4 in Table 5).

Zinc leaching after each catalytic cycle was also investigated for catalyst of Example A1, [SiO$_2$]—(CH$_2$)$_3$—O—(CH$_2$)$_2$—COOZn[Y]. As indicated in Table 6, zinc leaching was found to be negligible after two catalytic cycles, with leaching values around 1 mol % with respect to the original [Zn] loading present in the reaction.

TABLE 6

[Zn] leaching in the methoxycarbonylation of 2,4-TDA.[a]

| Entry | Substrate | Cycle | Leaching (mol % [Zn]) [b] |
|---|---|---|---|
| 1 | 2,4-TDA | #1 | ≤1.1 |
| 2 | 2,4-TDA | #2 | ≤0.8 |

[a][Zn] content determined by complexometric titration with EDTA as reagent and Eriochrome T as final point indicator.
[b] Leaching expressed as mol % [Zn] respect to the initial Zn content in the catalyst.

Summary of Examples B.2 to B.6

Total conversion of the substrates was observed for almost each combination of substrate and catalyst. The different catalysts prepared within this co-operation performed similarly in the alkoxycarbonylation of aniline. The four explored catalysts gave excellent results, with an average yield of 94% towards the corresponding carbamate.

The invention claimed is:

1. A silica-based zinc compound of the formula

[SiO$_2$]—CH$_2$—CHR—X—COOZn[Y]

wherein [SiO$_2$] represents a silica carrier selected from the group consisting of ordered mesoporous silica and irregular amorphous narrow pore silica, said silica carrier [SiO$_2$] being covalently bound to the terminal CH$_2$ group of CH$_2$—CHR—X—COOZn[Y];
R represents a moiety selected from the group consisting of hydrogen, —CH$_3$, and —CH$_2$CH$_3$;
X is an aliphatic chain of 2 to 11 carbon atoms that comprises one or more ether moieties; and
[Y] represents a mono anion.

2. The silica-based zinc compound according to claim 1, wherein X is an aliphatic chain of 2 to 9 carbon atoms that comprises one or more ether moieties.

3. The silica-based zinc compound according to claim 2, wherein X is CH$_2$—O—(CH$_2$)$_2$—.

4. The silica-based zinc compound according to claim 1, wherein said compound
(a) has a structure A in which the mono anion [Y] comprises a carboxylate group, the carboxylate oxygen atoms coordinating to the zinc atom and the carboxylate carbon atom being covalently connected to the silica carrier [SiO$_2$] via a chain of the same structure as CH$_2$—CHR—X, or
(b) has a structure B in which the mono anion [Y] is not covalently connected to the [SiO$_2$] carrier, or
(c) exists as a mixture of structures A and B.

5. The silica-based zinc compound according to claim 4, wherein the mono anion of structure B is selected from the group consisting of chloride, bromide, iodide, acetate, naphthenate, octanoate, propionate, salicylate, pivalate, acrylate, p-chlorobenzoate, phenolate, formate, chloroacetate, acetylacetonate, oxalate, and trifluoroacetate.

6. The silica-based zinc compound according to claim 5, wherein the mono anion of structure B is acetate.

7. The silica-based zinc compound according to claim 1, wherein the ordered mesoporous silica is selected from the group consisting of SBA-1, SBA-2, SBA-3, SBA-6, SBA-8, SBA-11, SBA-12, SBA-15, SBA-16, MCM-41, MCM-48, and FSM-16, and the irregular amorphous narrow pore silica is a silica gel with an average pore diameter in the range of 2.5 nm to 7.5 nm, and particle sizes in the range of 35-500 µm.

8. A method for producing the silica-based zinc compound according to claim 1, comprising:
A) reacting an unsaturated carboxylic acid of the formula CH$_2$=CR—X—COOH, where R represents a moiety selected from the group consisting of hydrogen, —CH$_3$, and —CH$_2$CH$_3$ and X is an aliphatic chain of 2 to 11 carbon atoms that comprises one or more ether moieties, with a trialkyloxy silane or triaryloxy silane or mixed alkyl-aryloxy trisubstituted silane in the presence of a catalyst to yield a silicon-containing addition product;

B) impregnating a silica carrier selected from the group consisting of ordered mesoporous silica and irregular amorphous narrow pore silica with a solution of the silicon-containing addition product in a solvent to yield a silica-based carboxylic acid; and
C) ion-exchanging the silica-based carboxylic acid with a zinc salt to yield the silica-based zinc compound.

9. The method according to claim 8, wherein the zinc salt is selected from the group consisting of zinc(II) chloride, bromide, iodide, acetate, naphthenate, octanoate, propionate, salicylate, pivalate, acrylate, p-chlorobenzoate, phenolate, formate, chloroacetate, acetylacetonate, oxalate, and trifluoroacetate.

10. A method of producing carbamate compounds, comprising reacting an organic amine with a dialkyl carbonate in the presence of a catalyst, wherein the catalyst is the silica-based zinc compound according to claim 1.

11. The method according to claim 10, wherein the dialkyl carbonate is selected from the group consisting of propyl carbonate, ethyl carbonate, and methyl carbonate.

12. The method according to claim 10, wherein the reaction of the organic amine with the dialkyl carbonate is carried out at a molar ratio of organic amine to Zn catalyst ranging from 10:1 to 20:1.

13. The method according to claim 10, wherein the reaction of the organic amine with the dialkyl carbonate is carried out at a temperature ranging from 150° C. to 200° C. for a reaction time ranging from 0.5 h to 6 h.

14. The method according to claim 10, wherein the organic amine is an aromatic amine selected from the group consisting of aniline, 2,4-diamino-N-phenylaniline, o-, m-, and p-phenylenediamine, 2,4-diaminotoluene, 2,6-diaminotoluene, 1,2,4,5-tetraaminobenzene, 4-methoxy-m-phenylenediamine, 4-amino-N-phenylaniline, 2-amino-N-methylaniline, N-isobutyl-p-phenyldiamine, o-, m-, and p-xylylenediamine, N-isoamyl-p-phenylenediamine, N-benzyl-p-phenylenediamine, N-cyclohexyl-p-diphenylenediamine, N,N'-di(n-propyl)-p-phenylenediamine, N-(n-butyl)-N'-benzyl-p-phenylenediamine, N,N'-dibenzyl-p-phenylenediamine, N-ethyl-m-phenylenediamine, N-ethyl-o-phenylenediamine, N-methyl-m-phenylenediamine, N,N'-diethyl-p-phenylenediamine, N-methyl-N-(n-propyl)-p-phenylenediamine, 4,4'-oxydianiline, 4,4'-ethylenedianiline, 2,4-bis(4-aminobenzyl)aniline, 4,4'-methylenebis(N,N-dimethylaniline); 4,4'-methylenebis(N-methylaniline); benzidine; N,N,N',N'-tetramethylbenzidine, bis(3,4-diaminophenyl)methane, bis(3-methyl-4-aminophenyl)methane, 2,2'-, 2,4'- or 4,4'-methylene dianiline, 1,6-hexamethylene diamine, isophorone diamine, (2-aminocylohexyl)-(4'-aminocylohexyl)-methane, bis-(4-aminocyclohexyl)-methane and mixtures of the aforementioned organic amines.

15. The method according to claim 14, wherein the organic amine is selected from the group consisting of aniline, 2,4-diaminotoluene, 2,6-diaminotoluene, and mixtures thereof or wherein the organic amine is selected from the group consisting of 2,2'-, 2,4'-, 4,4'-methylene dianiline, and mixtures thereof.

* * * * *